United States Patent [19]

Wann et al.

[11] Patent Number: 5,310,672

[45] Date of Patent: May 10, 1994

[54] INDUCTION OF SOMATIC EMBRYOGENISIS IN TAXUS, AND THE PRODUCTION OF TAXANE-RING CONTAINING ALKALOIDS THEREFROM

[75] Inventors: Steven R. Wann, Lawrenceville, N.J.; William R. Goldner, Langhorne, Pa.

[73] Assignee: Union Camp Corporation, Wayne, N.J.

[21] Appl. No.: 102,517

[22] Filed: Aug. 5, 1993

Related U.S. Application Data

[63] Continuation of Ser. No. 860,712, Apr. 1, 1992, abandoned.

[51] Int. Cl.$^5$ .......................... C12N 5/00; C12P 17/02
[52] U.S. Cl. ................................ 435/240.45; 435/123
[58] Field of Search ............. 435/172.3, 240.4, 240.45, 435/252.3, 123; 600/DIG. 49; 935/52, 67

[56] References Cited

U.S. PATENT DOCUMENTS

| | | | |
|---|---|---|---|
| 4,886,937 | 12/1989 | Sederoff et al. | 800/1 |
| 4,957,866 | 9/1990 | Gupta et al. | 435/240.4 |
| 5,019,504 | 5/1991 | Christen et al. | 435/123 |
| 5,024,944 | 6/1991 | Collins et al. | 435/172.3 |
| 5,034,326 | 7/1991 | Pullman et al. | 435/240.4 |
| 5,036,007 | 7/1991 | Gupta et al. | 435/240.45 |
| 5,041,382 | 8/1991 | Gupta et al. | 435/240.45 |

OTHER PUBLICATIONS

Page-DeGivry M. Thile (1973) Z. Pflanzenphysiol. Bd. 705, pp. 406–413.
Dekeyser, R. A. et al. (1990) the Plant Cell 2:591–602.
Neuhaus, G. et al. (1987) theor. Appl. Genet. 75:30–36.
Yibrah, H. S. et al. (1990) Plant Physiol 79(2, part 2) A38.
Kueh et al. (1981) Planta 153:166–171.
Ellis et al. (1991) Applications of Biotechnology to Tree Culture Protection and Utilization, Abstract.
Becwar, M. R. et al., "Somatic Embryo Development and Plant Regeneration from Embryogenic Norway Spruce Callus", in *Forest Biology*, pp. 155–160, from *Tappi Journal* 70(4) (Apr. 1987).
Bernard-Dagan, C., "Biosynthesis of Lower Terpenoids: Genetic and Physiological Controls in Woody Plants", in *Genetic Manipulation of Woody Plants*, Hanover and Keathley, eds., Plenum Press, pp. 329–351 (1987).
Borman, S., "Scientists Mobilize to Increase Supply of Anticancer Drug Taxol", *C&EN*, pp. 11–18, (Sep. 2, 1991).
Dougall, D. K. et al., "Taxol (NCS 125,973) Production by Cell Culture", SSIE Abstract No. 1CA 27139 2 (1979).
Durzen, D. J. et al., "Somatic Embryogensis and Polyembryogenes is in Doulgas-Fir Cell Suspension Cultures", *Plant Science* 52:229–235 (1987).
Edgington, S. M., *Biotechnology* 9:933–938 (Oct. 1991).
Fett-Neto, A. G. et al., "Cell Culture of *Taxus* as a Source of the Antineoplastic Drug Taxol and Related Taxanes", *Biotechnology* 10:1572–1575 (Dec. 1992).
Gupta, P. K. et al., "Biotechnology of Somatic Polyembryogenesis and Plantlet Regeneration in Lobiolly Pine", *Biotechnology* 5:147–151 (Feb. 1987).
Nabors, M. W. et al., "Long-Duration, High-Frequency Plant Regeneration from Cereal Tissue Cultures", *Planta* 157:385–391 (Springer-Verlag 1983).
Nagmani, R. et al., "Single-Cell Orgin and Development of Somatic Embryos in *Picea abies* (L.) Karst. (Norway Spruce) and P. glauca (Moench) Voss (White Spruce)", *Plant Cell Reports* 6:157–159 (1987).

(List continued on next page.)

Primary Examiner—David T. Fox
Assistant Examiner—Elizabeth F. McElwain
Attorney, Agent, or Firm—Sterne, Kessler, Goldstein & Fox

[57] ABSTRACT

The present invention provides methods of inducing somatic embryogenesis in tissue cultures derived from varieties of Taxus. In addition, the present invention provides methods of obtaining taxol, or precursors thereof, using in vitro propagated somatic embryo tissues.

6 Claims, 4 Drawing Sheets

OTHER PUBLICATIONS

Rohr, R. et al., "Ultrastructural Changes in Haploid Embryoids of Larix Decidua During Early Embryogenesis", *Amer. J. Bot.* 76(10):1460–1467 (1989).

Tautorus, T. E. et al., "Somatic Embryogenesis in Conifers", *Can. J. bot.* 69:1873–1899 (1991).

Vidensek, N. et al., "Taxol Content in Bark, Wood, Root, Leaf, Twig, and Seedling from Several *Taxus* Species", *J. Natural Products* 53(6):1609–1610 (Nov.–Dec. 1990).

Wann, S. R. et al., "Biochemical Differences Between Embryogenic and Nonembryogenic Calli of Conifers", *Trees*3:173–178 (Springer–Verlag 1989).

Wann, S. R. et al., "Biochemical Differences Between Embryogenic and Nonembryogenic Callus of *Picea abies* (L.) Karst", *Plant Cell Reports* 6:3914 42 (Springer–Verlag 1987).

Wann, S. R. et al., "Norway Spruce as a Model System for Somatic Embryogenesis in Conifers", *Proceedings–Tappi, Research and Development Conference*, Raleigh, NC, pp. 131–136 (1986).

Feirer, R. et al., The Occurrence of Proplastids in Somatic Embryos of Norway Spruce and Carrot, Ann. Meeting of the American Society of Plant Physiologists (1987).

Feirer, R. P., Chloroplast Ultrastructure and Gene Expression in Embryogenic Conifer Callus, in *Proceedings IUFRO*, Molecular Genetics Working Group Conference, Chalk River, Ont., pp. 89–95 (1987).

Feirer, R. P., Biochemical and Ultrastructural Studies of Somatic Embryogenesis of Carrot (Daucus Carota L.) Inbreds, Diss. Abstr. Int. B Order No. DA8901163 (1989).

Lewis, N. R. and Croteau, R., Taxol Biosynthesis, from Proceedings: Second National Cancer Institute Workshop on Taxol and *Taxus*, Alexandria, VA (Sep. 1992).

Thiel, K. A., "Escagenetics Receives Second Taxol Patent", *BioWorld Today*, p. 3, Monday, Jan. 17, 1994.

| \multicolumn{5}{c}{SUMMARY OF CULTURE INITIATION FROM IMMATURE EMBRYOS OF TAXUS GENOTYPES, 1991} |

| Genotype | Origin | Collection Date | Embryos Cultured No. | Embryogenic Cultures No. (%) |
|---|---|---|---|---|
| T. brevifolia | Special Trees (Corvallis, OR) | July 10 | 55 | 14(25) |
| T. baccata | Longwood Gardens (Kennett Square PA) | August 10 | 10 | 3(30) |
| T. x media cv. "Hicksii" | " | " | 8 | 3(38) |
| T. cuspidata cv. "Thayerae" | " | " | 9 | 3(33) |
| T. baccata cv. "rependens" | " | August 28 | 34 | 5(15) |
| T. x media | U.S. Nat'l Arboretum (Washington, D.C.) | September 16 | 8 | 3(38) |
| T. x media cv. "Flushing" | " | " | 12 | 4(33) |
| T. x media cv. "Hicksii" | " | " | 12 | 4(33) |
| T. cuspidata cv. "Thompson" | " | " | 4 | 0 |
| T. cuspidata | " | " | 8 | 1(13) |
| TOTAL EMBRYOGENIC LINES = 40 | | | | |

Trace 3

FIG. 4B

Trace 2

FIG. 4C

Trace 1

5,310,672

INDUCTION OF SOMATIC EMBRYOGENISIS IN TAXUS, AND THE PRODUCTION OF TAXANE-RING CONTAINING ALKALOIDS THEREFROM

This application is a continuation of application Ser. No. 07/860,712, filed Apr. 1, 1992, now abandoned.

FIELD OF THE INVENTION

The invention is in the field of plant cell culture and pharmacology. In particular, the invention relates to the induction of somatic embryogenesis in plant tissue cultures and primary explants of the genus Taxus, specifically *T. brevifolia*.

The invention further relates to the surprising discovery that somatic embryos induced from explants of *T. brevifolia* produce taxane-ring containing alkaloids. Utilizing this observation, methods are described for the production of taxol and taxol precursors from in vitro propagated cultures of somatic embryos.

BACKGROUND OF THE INVENTION

A. Taxol and the production of secondary plant metabolites in vitro

Taxol, a diterpene, was first identified in 1964 and has subsequently been shown to have anti-cancer activity against ovarian cancer, breast cancer, small-cell lung cancer, melanoma, and colon cancer.

Taxol is produced primarily in the bark and cambial tissue of the pacific yew *Taxus brevifolia*. Using current purification procedures, 1 kilogram of taxol requires processing of approximately 10,000 kilograms of bark. This is equivalent to 2,000–4,000 sixty to seventy year old trees. Recent estimates put the need of taxol at approximately 250 kilograms of the purified drug per year. This is equivalent to a yield of 25 million kilograms of dried bark or approximately 750,000 trees. Due to the shortage of the pacific yew, other sources of taxol are currently being sought.

One potential source of taxol which has been examined is in vitro cultured plant cells and tissues. U.S. Pat. No. 5,019,504 describes the initiation and proliferation of callus cell cultures from explants of *T. brevifolia*. The callus cells produced by this procedure were shown to produce taxol.

There are several obstacles to the use of callus or undifferentiated cell cultures as a means of producing secondary metabolites such as taxol. Typically, secondary metabolites are produced by specialized or differentiated tissues; most notably bark in the case of taxol, or leaves in the case of other taxanes such as baccatin. Undifferentiated, or callus cultures often lack the necessary biosynthetic capacity to assemble molecules as complex as taxanes, or, the degree of cytodifferentiation required to sequester these molecules once synthesized. The result has been that most secondary metabolites are not found in callus cultures, and, in cases where they have been detected in callus, the concentration is usually very much lower than that in planta.

Nevertheless, callus cultures have been extensively investigated for the production of secondary metabolites due to their ease of establishment, manipulation and rapid growth rate. Often, for investigations in vitro, rapidly-growing callus cultures are the most convenient way to produce the large quantities of tissue required for detection of secondary metabolites such as taxol that are found in such low concentrations. The rapid growth rate of callus cultures underscores another of their disadvantages in that the cells that comprise these cultures tend to be genetically unstable, demonstrating high levels of genetic recombination and unstable ploidy levels. Such genetic instability can ultimately lead to cultures with diminished taxol production capacity. In order to avoid this problem, callus cultures need to continually be reestablished from a genetic stock.

For the large scale production of secondary plant products in vitro, it would be desirable to combine the rapid growth rates and capacity for high biomass concentrations of undifferentiated cell culture systems with the inherent capacity for secondary metabolite production of differentiated cells or tissues. Researches have realized the potential for secondary metabolite production in cultures that proliferate in a manner akin to undifferentiated cell cultures (i.e., callus or cell suspension), but are instead comprised of differentiated cells or tissues. For example shoot cultures (tissue cultures comprised of masses of rapidly proliferating shoots) have been investigated as sources of essential oils and alkaloids that are found in leaf or stem tissue (Heble, in *Primary and Secondary Metabolism in Plant Cell Cultures*, Neumann et al. (ed.), Springer-Verlag, Berlin Heedelberg, pp.281-289 (1985)). In shoot cultures, the specific tissue types that produce and sequester essential leaf oils are multiplied, and the rigid developmental program required for shoot morphogenesis also minimizes genetic instability. In this way, tissue cultures have been shown to combine the attractive features of both undifferentiated and differentiated systems.

Although taxol has been detected in undifferentiated cell culture systems, its production has not been described in tissue culture systems. One such system is embryogenic tissue cultures.

Embryogenic conifer tissue cultures are strikingly dissimilar to conifer callus cultures biochemically, histologically, and in macroscopic appearance. Although the term "callus" is a generic term used to describe cell and tissue cultures, many researchers in the field of conifer somatic embryogenesis object to the use of "callus" in describing embryogenic conifer tissue (See for example Gupta and Durzan, *Bio/Tech.* 5:147-151 (1987); Rohr et al., *Amer. J. Bot.* 76:1460-1467 (1988); Tautorus et al., *Can. J. Bot.* 69:1873-1899 (1991)). The reason for the objection to the use of the term "callus" is that, rather than being comprised of undifferentiated cells, embryogenic conifer tissue cultures are comprised of differentiated cells (suspensor-like cells) and structures analogous to early stage embryos found in developing seeds. Therefore, embryogenic conifer tissue cultures do not fit the detention of callus or their liquid counterparts, cell suspension cultures, and represent an improved way to produce taxol by the embodiment of the beneficial growth characteristics of cell culture systems with the capacity for secondary metabolite production of tissue culture systems.

B. Somatic Embryogenesis in Conifers

Although procedures for the induction of somatic embryogenesis have been known in the art for some time (Tisseral et al,. *Hort. Re*.1:1–78 (1979)), it has only been recently demonstrated successfully with coniferous species (See Hakman et al. *Plant Sci.* 38:53–59 (1985)). Since the first reports of successful induction of somatic embryogenesis in conifer cell cultures, eighteen (18) species from the genera Pinus, Picea, Abies, Larix, and Psuedotsuga (Tautorus et al., *Can. J. Bot.*

69:1873–1899 (1991)), have been demonstrated as having the capacity to produce somatic embryos.

The production of somatic embryos from conifers is not universal. Several important varieties have yet to be successfully cultured, such as members of the genus Taxus.

C. Transgenic Plants.

Recent advances in recombinant DNA and genetic technologies have made it possible to introduce and express a desired gene sequence in a recipient plant. Through the use of such methods, plants have been engineered to express gene sequences that are not normally or naturally present in the native plant, or to exhibit altered expression of naturally occurring genes. Plants produced through the use of recombinant techniques are known as "transgenic" plants.

Transgenic plants are generally produced by transforming a single plant cell and then regenerating a whole plant from the cell via somatic embryogenesis. Since many genera of plants have been regenerated from a single cell (Friedt, W. et al. *Prog. Botany* 49:192–215 (1987); Brunold, C. et al., *Molec. Gen. Genet.* 208:469–473 (1987); Durand, J. et al., *Plant Sci* 62:2-63–272 (1989); Attree et al., *Can. J. Bot.* 67:1790–1795 (1989)), successful production of transgenic plants from a wide variety of plant groups is theoretically possible.

Several methods have been developed to deliver and express a foreign gene into a plant cell. These include engineered Ti plasmids from the soil bacterium *A. tumefaciens* (Czako, M. et al., *Plant Mol. Biol.* 6:101–109 (1986); Feirer et al., *Proceedings 20th Southern Forest Tree Improvement Conference*, Jun. 26-30, 1989, Charleston, S.C., pg. 381; Jones, J. D. G. et al., *EMBO J.* 4:2411–2418 (1985), engineered plant viruses such as the cauliflower mosaic virus (Shah, D. M. et al., *Science* 233:478–481 (1986)); Schewmaker, C. K. et al., *Virol.* 140:281–288 (1985)), microinjection of gene sequences into a plant cell (Crossway, A. et al., *Molec. Gen. Genet.* 202:179–185 (1986); Potrykus, I. et al., *Molec. Gen. Genet.* 199:169–177 (1985)), electroporation (Fromm, M.E. et al., *Nature* 319:791–793 (1986); Tautorus et al., *Theor. Appl. Genet.* 78:531–536 (1989), and DNA coated particle acceleration (Bolik, M. et al. *Protoplasma* 162:61–68 (1991)). Several of these procedures have been successfully employed to transform conifer tissues in vitro. (Ellis et al., *International Society of Plant Molecular Biology*, meeting of Oct. 6-11, 1991, Tucson, Ariz.).

SUMMARY OF THE INVENTION

For the production of taxol and related taxanes, embryogenic tissue cultures of conifers (i.e., Taxus) combines the attractive growth rate and biomass production capabilities of callus cultures with the capacity for secondary metabolite accumulation inherent to differentiated cells. Although taxol was detected in callus cultures of *T. brevifolia* (Christen et al., U.S. Pat. No. 5,019,504) the yield has not been reported. Embryogenic tissue cultures of Taxus grow like, and can be handled in the same way, as conventional callus cultures, but have the capacity for a greater yield of taxanes as they contain tissues with the ability to produce and sequester taxanes.

Embryogenic conifer tissue is a unique tissue type even to the field of somatic embryogenesis, and the potential of this material in plant propagation and secondary metabolite production has not been appreciated. Therefore, the present invention provides a description of how the unique capabilities of embryogenic tissue cultures of Taxus may be used to produce taxol and related taxanes.

The present invention is based on the observation that in vitro cultured primary explants obtained from plants of the genus Taxus, produce and secrete compounds which inhibit somatic embryogenesis. Based on this observation, the present invention provides methods of inducing somatic embryogenesis from cultures and primary explants of Taxus. Specifically, embryogenic tissue can be obtained from explants of the genus Taxus by first culturing a Taxus explant in a culture media and, second, successively transferring the explant to fresh media during culture to obtain early stage somatic embryos.

The present invention is further directed to cultured Taxus embryogenic tissue.

The present invention further provides methods of clonally propagating plants from the genus Taxus. Specifically, plants of the genus Taxus can be clonally propagated by (1) culturing a Taxus explant in a culture media, (2) successively transferring the explant to fresh media during culture to obtain embryogenic tissue, and (3) transferring embryogenic tissue to media capable of inducing the somatic embryos contained therein into plants.

The present invention further provides methods of producing genetically altered plants of the genus Taxus. Utilizing the methods of the present invention for the induction of somatic embryogenesis, it is now possible to regenerate whole plants from a genetically altered, single Taxus cell. Plants produced in this fashion can be selected for their ability to produce elevated levels of taxol or taxane-ring containing alkaloids, or for the ability to grow under specific physiological conditions. Specifically, the present invention is related to methods of generating variant plants of Taxus which overproduce taxane-ring containing alkaloids. These variants can be selected from naturally occurring variants which appear during in vitro propagation, generated through chemical or physical mutagenesis, or obtained as a result of being transformed with an exogenously supplied DNA.

The present invention is additionally based on the surprising observation that in vitro propagated somatic embryos of Taxus produce taxane-ring containing alkaloids. This result is surprising because taxol has not been reported to occur in embryos. Moreover, it would not have been expected that a secondary metabolite such as taxane-ring containing alkaloids could have been produced in somatic embryos, since such embryos are believed to lack the requisite biochemical machinery for producing such secondary metabolites.

Utilizing in vitro cultures of embryogenic tissue, it is now possible to produce large amounts of taxane-ring containing alkaloids. Embryogenic tissue offers the advantages of the rapid growth rate associated with callus cultures for the production of large quantities of tissue, while at the same time affords the proliferation of structures (somatic embryos) that sequester taxanes. Taxane-ring containing alkaloid compounds from somatic embryo cultures of Taxus can be obtained by first culturing explants from the genus Taxus in a culture media under conditions which produce somatic embryos, and second, isolating the taxane-ring containing alkaloid compounds from the somatic embryos or the culture media.

DETAILED DESCRIPTION OF THE INVENTION

I. Induction of Somatic Embryogenesis in Explants From Varieties Of Taxus

Figure 3:
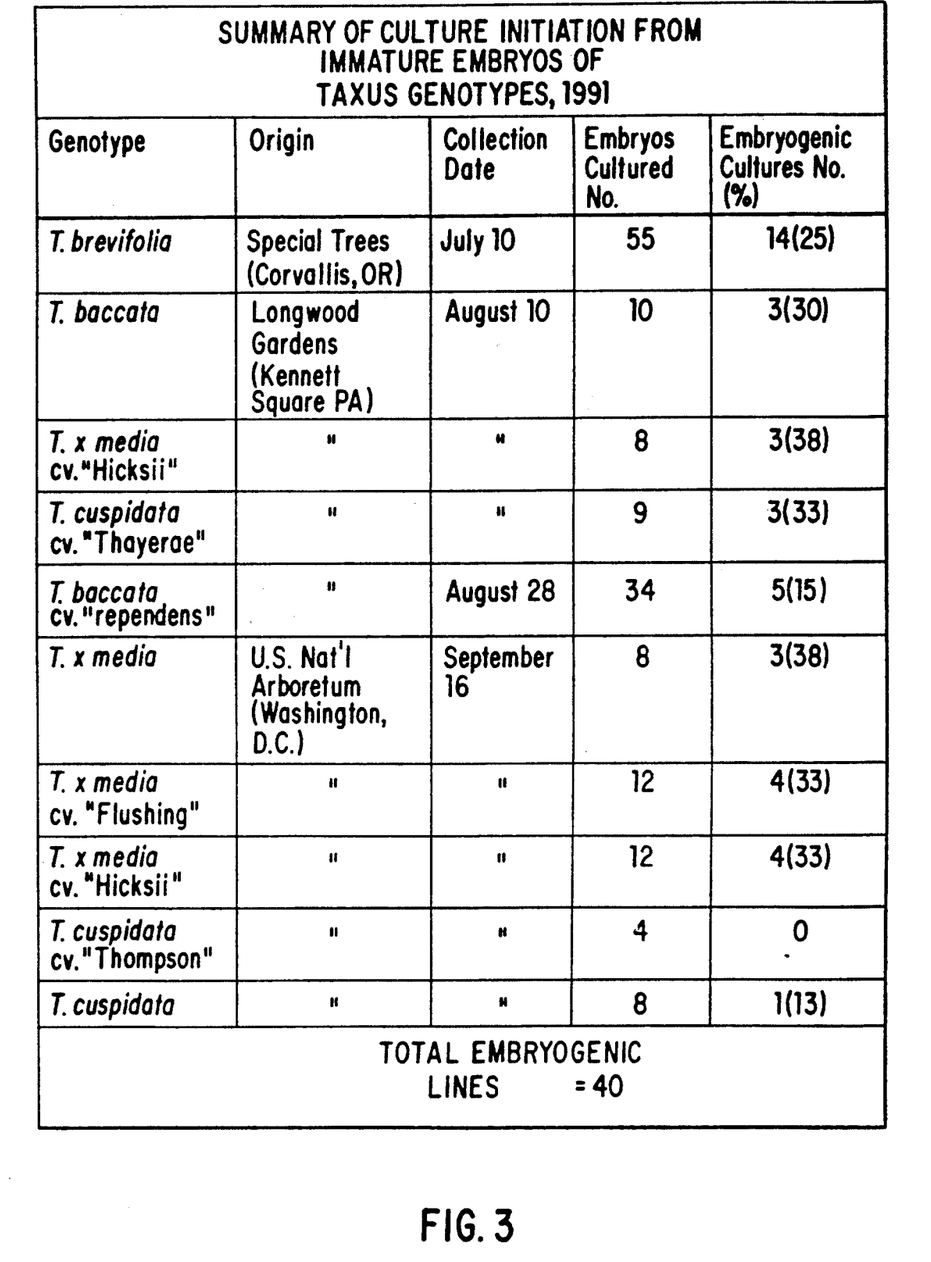
FIG. 3 shows a summary of induction of somatic embryogenesis from a number of varieties of Taxus.

The present invention is based on the observation that primary explants and in vitro cell cultures derived from plants of the genus Taxus, especially *T. brevifolia*, produce compounds which inhibit somatic embryogenesis. Based on this observation, it can be inferred that taxane-ring containing alkaloids are being produced. Thus, the present invention provides methods of inducing somatic embryogenesis from primary explants of varieties of Taxis, especially *T. brevifolia* (FIG. 3).

Specifically, the method comprises the steps of: culturing an explant from a plant of the genus Taxus in a media capable of promoting the induction of somatic embryogenesis, transferring the explants to fresh media during culturing to remove the cultured cells from the inhibitors which are produced, and isolating the somatic embryos produced in the culture.

Figure 1:
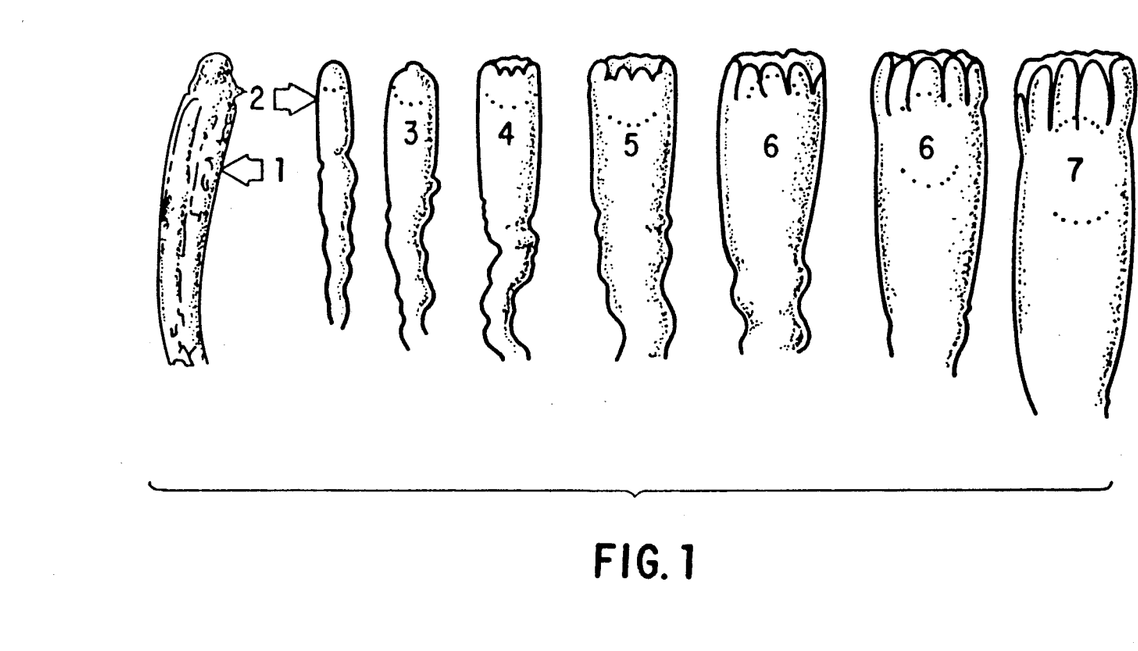
FIG. 1 shows the typical stages of development of embryos in the Coniferales.

As used herein, a "somatic embryo" consists of a cell or group of cells having the potential to become a plant by developing along a route that mimics the course of development a zygotic embryo undergoes, within a seed. In conifers, as in most plants, somatic embryogenic cells can be classified into two stages (FIG. 1). The first stage consists of proembryogenic masses and early-formed somatic embryos (see stage 1 in FIG. 1), and the second stage consist of further differentiation and development of the early-formed embryos to embryos (stage 3-6). The pro-embryogenic mass is a group of cells having the potential to become an embryo but lacking defined meristematic organ primordia. It is these rudimentary stages of embryo development that proliferate as long as the cultures are maintained on media with 2, 4-D, and BA.

Upon transfer of embryogenic tissue cultures to a medium that supports embryo maturation, embryo development proceeds along a pathway analogous to that found in seeds. The stages in this pathway are illustrated in FIG. 1.

By the final stage of embryogenesis (Stage 7), ripe, cotyledonary embryos are produced which possess a well defined elongated bipolar structure containing a latent meristem and cotyledon primordial at one end and a potential radical at the opposite end. Cells within these embryos are typically characterized as containing seed storage proteins, lipids, and are cytoplasmically dense.

Embryogenic conifer tissue differs significantly from callus cell cultures and many have argued that they cannot be called callus cultures. Callus cultures are considered to be an unorganized growth of undifferentiated cells that are either unconnected or loosely connected and can be generally produced by culturing a variety of explants. Unlike cells found in embryogenic cultures, callus cells tend to be spherical, isodiametric, highly vacuolated with non-dense cytoplasms. Callus cells are considered to be de-differentiated or undifferentiated plant cells since they are driven from the rapid cell division of differentiated plant explants.

Embryogenic tissue, on the other hand, is comprised of masses of (1) very early stage embryos, (2) cells in the process of producing early stage embryos (i.e. proembryogenic masses) or (3) suspensor-type cells that have been sloughed off by the early-stage embryos. Therefore, the cultures have an aspect of organization to them, as well as consisting of cell and tissue types, that are strikingly dissimilar by inspection under a low power microscope.

In addition to physical appearance, callus cells and embryogenic cells are different at the biochemical and histological level as indicated by differences in a number of biochemical markers such as ethylene evolution rate, concentrations of glutathione, the ability to reduce ferric ion, protein synthesis rates, and plastid structure. (Wann et al., *Plant Cell Reports* 6:39–42 (1987); Wann et al., *Trees* 3:173–178 (1989)).

As used herein, a "primary explant" is any tissue or cells obtained from a plant. This includes, but is not limited to, zygotic embryo tissue, root or shoot meristematic tissue, and cambium tissue. The most preferred tissue is obtained from immature arils and consists of zygotic embryos, as well as cotyledonous, and hypocotyledonous cells.

Any Taxus variety can be used as a source of the explant. This includes, but is not limited to, *T. brevifolia, T. baccata, T. x media*, and *T. cuspidata*.

Prior to culturing, the explant is surface sterilized to kill potential contaminants such as bacteria or fungus which may be present on the explant surface. The most commonly employed method involves immersion of the explant in a solution of bleach and a wetting agent such as Tween-20 TM. Such as immersion sterilizes the surface of the explant while not effecting the underlying cells. A vaccum can be employed during immersion in order to aid the sterilant in surface penetration. Once the explant has been obtained and treated, it is placed in a liquid or on solid culture media.

In general, most plant growth media which have been shown to be effective in inducing somatic embryogenesis in other conifers can be utilized in generating somatic embryos from varieties of Taxus. These include, but are not limited to BLG (Wann et al., *Trees* 3:173-178 (1989) herein incorporated by reference), MS (Gupta et al. *Bio/Technology* 5:141 (1987) herein incorporated by reference), BMI (Krogstrup, *Can. J. For. Res.* 16:664–668 (1986) herein incorporated by reference), and DCR (Gupta et al. *Plant Cell. Rep.* 4:177 (1985) herein incorporated by reference). Most preferred are medias which contain the plant hormones 2,4-dichlorophenoxyacetic acid (2,4-D) and benzyl adenine (BA) as well as casein hydrolysate. One skilled in the art will can readily adapt such medias for use in the present invention without undue experimentation. In the example provided below, BLG media is employed.

Various conditions may be employed in the culturing of the primary explants. Conditions such as temperature and lighting will vary slightly from plant variety to plant variety as well as tissue source. For *T. brevifolia*, culturing is most preferably performed in the dark and from about 20°–25° C. One skilled in the art will readily vary culture conditions to optimize both cell proliferation and embryo production.

The length of time an explant needs to be cultured before somatic embryogenesis is induced will vary depending on the source of the explant, culture conditions, and frequency of transfer. For immature embryo explants of *T. brevifolia*, cultured in BLG-casein media at 22° C., no light, with transfers from about every two to four weeks, embryogenic tissue will be induced in about 6 weeks.

As used herein, "transferring said explant" refers to the process of supplying fresh media to the explant. Transferring effectively removes the explant from the inhibitors of embryogenesis which are secreted by varieties of Taxus. This need for transferring in order to induce and maintain somatic embryogenesis is unique amongst conifers.

Procedures for transferring the cultured tissue will vary depending on the type of media employed. When the explant is maintained on solid media, transferring entails the removal of the explant from the old media to a new media. The inhibitors of embryogenesis produced by growing cultures of Taxus do not rapidly diffuse through solid media. Therefore, the explant may be removed from the secreted inhibitors by simply placing the cultured explant on a fresh surface of the culture plate.

Figure 2A:
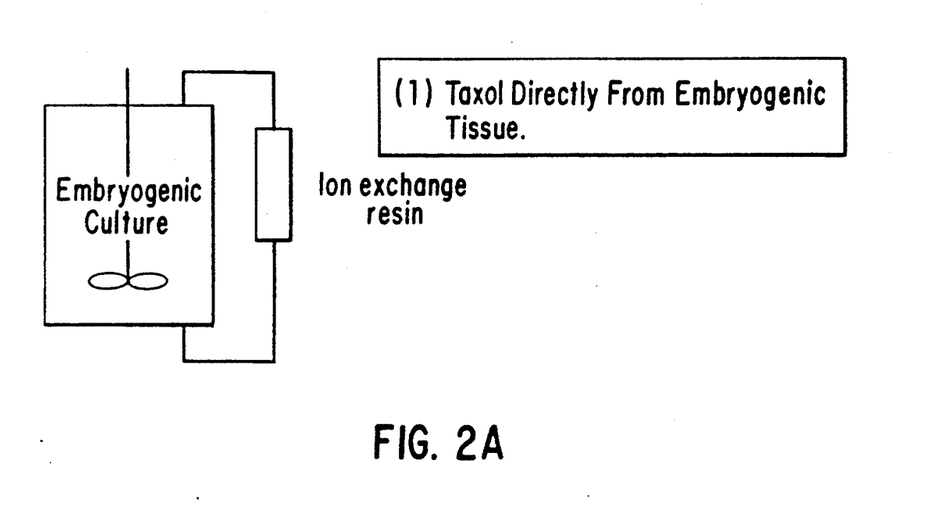
FIGS. 2a and 2b show a continuous flow liquid culture system for the production of somatic embryo (a) and taxane-ring containing alkaloids (b).

Somatic embryogenesis may also be induced in liquid cultures of Taxus. Embryogenic tissue can be removed from the liquid media via filtration or sedimentation to allow fresh media to be supplied. Alternatively, a continuous flow system can be employed to supply the cultured tissue with fresh media. In such a system, the tissue is maintained in an environment that allows media to flow through the environment while restricting the flow of the cultured cells (See FIG. 2a).

The length of time between transfers will vary depending on the source of the explant, culture conditions, media, as well as the cell density in the culture. In general, when solid media is employed, such transfer will for performed about every 2–3 weeks. One skilled in the art will be readily able to determine the time between transfer by visually observing the rate of production of somatic embryos.

Once a culture producing somatic embryos is obtained, the embryos can be matured, isolated and germinated to form seedlings. Any procedure known in the art for embryo maturation can be employed. These typically involve a transfer of embryogenic tissue to a medium with increased osmolarity and containing abscisic acid (ABA). (See Becwar et al., *Tappi Journal* 70(4):155–160 (1987)).

The present invention further provides cultured Taxus embryogenic tissue. Such tissue is obtained using the methods described above. Any Taxus variety can be utilized. This includes, but is not limited to *T. brevifolia, T. baccata, T. x media,* and *T. cuspidata.*

Utilizing the techniques described above, plants from the genus Taxus can now be clonally propagated from somatic embryos.

A plant from which clonal offspring is desired, may be used as a source of the primary explant. Through successive culture transfers, somatic embryogenesis of the primary explant can be induced as described above. The embryos thus produced can be readily regenerated into whole plants and thus generate plants which are clonally derived from the explant. (See Becwar et al., *Tappi Journal* 70(4):155–160 (1987); Durzan et al., *Plant Science* 52:229–235 (1987); Krogstrup et al., *Plant Cell Reports* 7:594–597 (1988), herein incorporated by reference).

Additionally, the above described methods can be used to propagate plants which are variants of the explant source.

As used herein, a "variant" is defined as any plant or tissue which contains a genetic alteration not present in the plant from which the explant is derived from. This may include a change in ploidy level, a change in the sequence of a particular segment of DNA, or the introduction of an exogenously supplied DNA sequence. The variant may be generated naturally during the process of tissue culturing, or can be generated through biochemical, physical, or molecular techniques.

Since plant cultures tend to be genetically unstable, naturally occurring variants may be produced during prolonged culture. Such variants can be assayed for a change in a physiological characteristic, such as accelerated growth, the level of production of a plant metabolite or alkaloid, or a change in ploidy level. Preferably, such variants will exhibit increased production of taxol or a taxol precursor. Once identified, the variant cell or cells can be isolated and used to produce clonally propagated plants with increased taxol or taxol precursor content as described above.

In addition to naturally occurring variants, variants may be generated through a variety of methods known in the art. These include, but are not limited to, physical or chemical mutagenesis, protoplast fusion, or direct transfer of exogenous DNA. Such methods can be used to induce variants in the primary explant prior to the initiation of somatic embryogenesis, or to the somatic embryos which have been generated using the methods described herein.

Physical or chemical mutagenesis entails exposing the cultured cells or primary explant to an agent which is capable of inducing DNA damage or inhibiting chromosome segregation during meiosis and mitosis. Such agents include UV light, ethylmethylsulfonate, nitrous oxide, acridine orange, colchicine, and nitrosoguanidine. Agents such as these have been employed in a variety of systems to introduce random changes in the DNA of the organism in order to generate variants. (Chaleff, R. S., *Science* 219:676–682 (1983)).

While the site of mutagenesis and the resulting variant produced is not predetermined, one skilled in the art can readily adapt known mutagenesis and selection procedures to the explants and embryogenic culture of the present invention.

The mutagenized cells may be screened for an alteration in the production of a secondary metabolite such as the taxane-ring containing alkaloids of the present invention. Preferably, such mutants will over produce the taxane-ring containing alkaloids. Methods for detecting the level of taxane-ring containing compounds include HPLC (See Examples) and by immunologically reacting a sample of the culture media with an antibody specific for such taxane-ring containing alkaloids. See Stephen M. Edington, *Bio/Technology* 9:933–938 (1991).

Protoplast fusion can be utilized to generate variants with increased ploidy levels as well as to produce plants containing chromosomes from other varieties. For example, by fusing a taxol or taxol-precursor producing variety of Taxus with a non-producing variety, a variant may be generated which processes the characteristics of both varieties.

Variants can also be produced through the introduction of exogenously supplied DNA. (Ellis et al., *International Society of Plant Molecular Biology*, meeting of Oct. 6–11, 1991, Tucson, Ariz.). As described earlier, numerous techniques have been developed to introduce DNA into a plant cell. These include, but are not limited to, engineered Ti plasmids from the soil bacterium *A. tumefaciens* (Czako, M. et al., *Plant Mol. Biol.* 6:101–109 (1986); Jones, J. D. G. et al., EMBO J. 4:2411–2418 (1985); Feirer et al., *Proceedings 20th Southern Forest Tree Improvement Conference*, Jun. 26–30, 1989, Charlestown, S.C., page 381), engineered plant viruses such as the cauliflower mosaic virus (Shah, D. M. et al., *Science* 233:478–481 (1986)); Shewmaker, C. K. et al., *Virol.* 140:281–288 (1985)), microinjection of gene sequences into a plant cell (Crossway, A. et al., *Molec. Gen. Genet.* 202:179–185 (1986); Potrykus, I. et al., *Molec. Gen. Genet.* 199:169–177 (1985)), electroporation (Fromm, M. E. et al., *Nature* 319:791–793 (1986); Tautorus, T. E. et al., *Theor Appl Genet* 78:531–536 (1989), Tautorus et al., *Theor Appl. Genet.* 78:531–536 (1989), and DNA coated particle acceleration (Bolik, M. et al. *Protoplasma* 162:61–68 (1991)).

Utilizing one of these procedures, one skilled in the art can readily generate a variant which contains an exogenously supplied gene construct. In such a fashion, a variant can be produced which contains a predetermined characteristic, such as resistance to an antibiotic. Screening for such a characteristic may be done routinely by those of ordinary skill in the art and without undue experimentation.

II. Taxane-Ring Containing Alkaloid Production in Embryonic Tissues

A further embodiment of the present invention is based on the observation that in vitro propagated somatic embryos of Taxus produces taxane-ring containing alkaloids. This is a surprising observation since taxol is normally sequestered in vacuoles and somatic embryos are not highly vacuolated. Moreover, it would not have been expected that a secondary metabolite such a taxane-ring containing alkaloid could be obtained from such biochemically immature cells. Utilizing such in vitro cultures, it is now possible to produce large amounts of taxane-ring containing alkaloids. In addition, it is now possible to produce Taxus seedlings on a large scale and isolate the taxane-ring containing alkaloids therefrom. This is significant since seedlings are second only to bark as a source of taxol and its precursors. (Vidensek, N. et al., *J. Natural Prod.* 53:1609–1610 (1990)).

Specifically, taxane-ring containing alkaloids can be obtained from cultures of somatic embryos derived from explants of the genus Taxus, especially *T. brevifolia*, *T. baccata*, *T. x media*, and *T. cuspidata*.

Figure 2B:
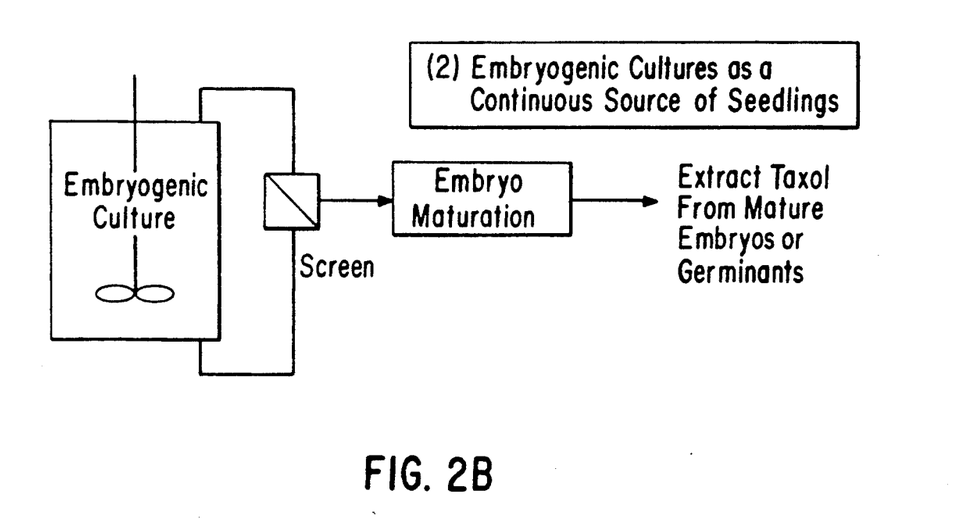

In detail, an explant is obtained from a variety of Taxus which produces the desired taxane-ring containing alkaloids. The explant is used to produce a culture which contains somatic embryos using the procedures described earlier. Taxane-ring containing alkaloids can then be isolated from either the culture media or from the tissue using techniques which are well known in the art such as column chromatography (See, Wani et al. *J. Am. Chem. Soc.* 93:2325 (1971); M. Boyd, Personal Communication (August 1991); (Witherup, K. M. et al., *J. Liq. Chromotgr.* 12:2117–2132 (1989)). One such system is shown in FIG. 2b.

Preferably, autoclaved fungal cells or extracts are added to the culture media to stimulate the production of taxane-ring containing alkaloids. When such fungal cell extracts are added to the media, the embryogenic tissue act to ward off the supposed infection by the production of the taxane compounds.

The most preferred embryos for isolating taxane-ring containing alkaloids are embryos from stage 7 and into germination. (See FIG. 1). Embryos from stages 1 and 2, though they may contain taxane-ring containing alkaloids, are hard to dissect and separate from non-embryogenic tissues. Embryos from stage 7 are easily separated from non-embryogenic tissues and therefore are preferred. One skilled in the art can readily adapt known procedures for isolating embryos in order to obtain any particular stage of embryo for use in the production of taxane-ring containing alkaloids.

Alternatively, fully developed seedlings produced from the embryogenic cultures, can be used as a source of the taxane-ring containing alkaloids.

The taxane-ring containing alkaloid can be isolated from media that is replaced batch-wise, or continuously. The embryogenic culture may be grown in free suspension or maybe immobilized within a carrier such as hollow fibers. Examples of such carriers are described in Durzan et al., *Plant Science* 52:229–235 (1987).

Having now generally described the invention, the same will be more readily understood through reference to the following examples which are provided by way of illustration, and are not intended to be limiting of the present invention, unless specified. All patents and publications cited herein are incorporated by reference herein in their entirety.

EXAMPLE

Procedure for the Initiation and Maintenance of Embryogenic Tissue in Taxus and its Subsequent Analysis for Taxol Initiation and maintenance of embryogenic Taxus tissue.

Immature arils of Taxus species were collected throughout the summer (the best time is July) and were sterilized by stirring with a 20% solution of household bleach (1.1% sodium hypochlorite) for 30 min. employing several drops of Tween 20 TM (per 100 mL sterilant) as a wetting agent. After three rinses with sterile water, immature embryos were aseptically excised from the arils and were plated horizontally onto the medium shown in Table 1. Cultures were incubated at 22° C. in the dark for four weeks. At the end of this time, the explants were transferred to fresh medium by simply moving the cultures to a new location on the original petri dish. After two additional weeks (total time=six weeks), the cultures were scored for the initiation of embryogenic tissue. Embryogenic tissue exhibited the translucent to white, mucilaginous phenotype characteristic of embryogenic conifer tissue.

Most often, embryogenic tissue originated in the cotyledon or hypocotyl region of the immature embryo explant. Embryogenic tissue was teased away from the original explant with a forceps and could thereafter be maintained as a purely embryogenic tissue culture on the same medium and under the same conditions described for initiation. Embryogenic tissue was serially maintained by transfer to fresh medium every three weeks.

The frequency of initiation of embryogenic tissue from immature Taxus embryos is illustrated for one particular collection (Corvalis, OR) of immature *Taxus brevifolia* seed (see Table 2). Embryos that were just at the stage of cotyledon formation gave rise to embryogenic callus at a higher frequency than younger embryos that had not yet developed to the cotyledonary stage (see FIG. 1). The inclusion of casein hydrolysate (500 ml/L) in the medium afforded not only a higher initiation frequency from cotyledonary stage embryos but also made the initiation of embryogenic tissue from younger embryos possible.

The frequency if initiation of embryonic tissue from cultures other than *T. brevifolia* is shown in FIG. 3. These include *T. baccata*, *T. x media* and *T. cuspidata*.

Extraction and determination of taxane-ring containing alkaloids from embryogenic tissue Taxol was analyzed in embryogenic tissue by a modification (M. Boyd, *Personal Communication* (August 1991)) of the published procedure (Witherup, K. M. et al., *J. Liq. Chromotgr.* 12:2117–2132, (1989)). Briefly, embryogenic Taxus tissue was homogenized in hexane in a Ten Breock tissue grinder. The hexane was discarded and the remaining plant tissue was extracted with 1:1 methylene chloride:methanol overnight at room temperature. The next day the mixture was filtered, and evaporated to dryness under a stream of nitrogen. The residue was dissolved in a minimal amount of methanol and was partitioned between 1:1 methylene chloride:water. The aqueous layer was discarded and the organic layer was evaporated to dryness. The residue was taken up in methanol and subjected to HPLC analysis.

HPLC analysis was performed using a phenyl bonded silica gel column operated under isocratic conditions employing a mobile phase consisting of (20:32:48) methanol:acetonitrile:50 mM aqueous ammonium sulfate buffer adjusted to pH 4.4 with acetic acid. The flow rate was 1 mL/mm and the effluent was monitored at 228 nm.

No taxol was observed being produced in embryogenic tissues containing proembryogenic masses and Stage 1 somatic embryos. However, several peaks were observed whose migration indicated that they are taxane-ring containing alkaloids other than taxol.

These results were confirmed using a polyclonal antibody-based indirect competitive inhibition enzyme immunoassay (CIEIA; Hawaii Biotechnology Group, Inc.).

TABLE 1

| Composition of Media used for Embryogenic Yew Tissue Cultures. | |
|---|---|
| Component | Concentration, mg/L |
| KNO3 | 100 |
| MgSO4.7H2O | 320 |
| KH2PO4 | 170 |
| CaCl2.2H2O | 440 |
| KCl | 745 |
| KI | 0.83 |
| H3BO3 | 6.2 |
| MnSO4.H2O | 16.9 |
| ZnSO4.7H2O | 8.6 |
| Na2MoO4.2H2O | 0.25 |
| CuSO4.5H2O | 0.025 |
| CoCl2.6H2O | 0.025 |
| FeSO4.7H2O | 27.8 |
| Na2 EDTA | 37.3 |
| Inositol | 100 |

TABLE 1-continued

| Composition of Media used for Embryogenic Yew Tissue Cultures. | |
|---|---|
| Component | Concentration, mg/L |
| Nicotinic acid | 0.5 |
| Pyridoxine | 0.1 |
| Thiamine.HCl | 0.1 |
| Sucrose | 20,000 |
| Glutamine | 1,450 |
| Asparagine | 100 |
| 2, 4-D | 2 |
| Benzyl adenine | 1 |
| Bacto agar | 8,000 |
| pH = 5.8 | |

BLG 2/1 medium = above formulation
BLCG 2/1 medium = above formulation + 500 mg/L casein hydrolysate

TABLE 2

INITIATION FREQUENCY OF SOMATIC EMBRYOGENESIS AS A FUNCTION OF IMMATURE EMBRYO DEVELOPMENT STAGE IN *TAXUS BREVIFOLIA* (6 weeks)

| Medium | Immature Embryo Stage (See below) | Embryos Cultured, No. | Embryogenic Callus, No. (%) |
|---|---|---|---|
| BLG 2/1 | 1-2 | 5 | 0 |
| | 3 | 10 | 0 |
| | 4-6 | 9 | 3 (33) |
| BLCG 2/1 | 1-2 | 6 | 0 |
| | 3 | 11 | 3 (27) |
| | 4-6 | 14 | 8 (57) |

Production of Taxol from Embryogenic Tissue Cultures of Taxus in Liquid Media

Taxol was not detected in embryogenic cultures of Taxus species that were maintained on agar-solidified, BLG-casein medium as just described. However, taxol was detected in the spent medium when embryogenic tissue was grown in liquid medium of the same composition in shake (110 rpm) flasks. Liquid cultures of embryogenic Taxus tissue were produced by dispersing masses of embryogenic tissue grown on agar-solidified medium in small volumes of liquid BLG-casein maintenance medium. After 1–2 months at 22° C., 110 rpm and an 8 h photoperiod under dim (80 foot-candles) fluorescent light, cultures consisting of small masses of tissue of uniform size were obtained. Until cultures of uniformly sized tissue masses were obtained, liquid media was replaced every 10–21 days by decanting spent medium and adding the same volume of fresh medium.

Figure 4A:
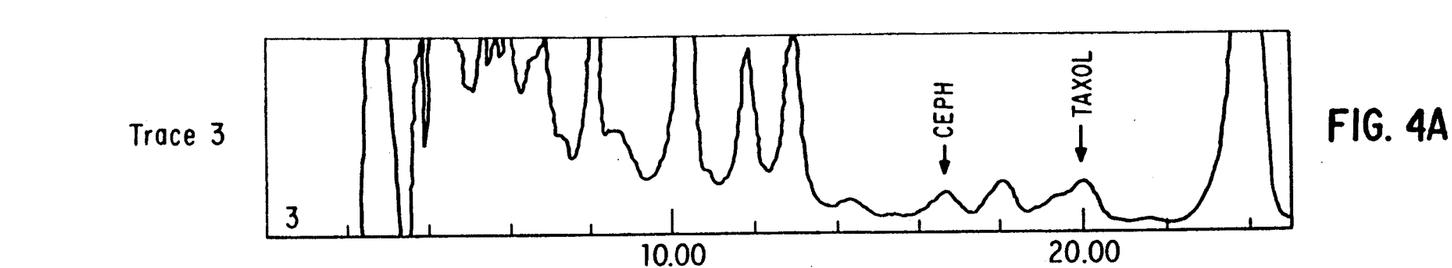
FIGS. 4A, 4B and 4C show a series of three HPLC traces, wherein trace 1 is an HPLC trace showing the separation of the components of an extract obtained by culture of *Taxus brevifolia* in liquid media. Trace 2 is an HPLC trace of a mixture of the *Taxus brevifolia* extract and a taxol standard (3:1; see the peak at about 20.00 minutes). Trace 3 is an HPLC trace of a 1:1 mixture of the extract and taxol standard.
Figure 4B:
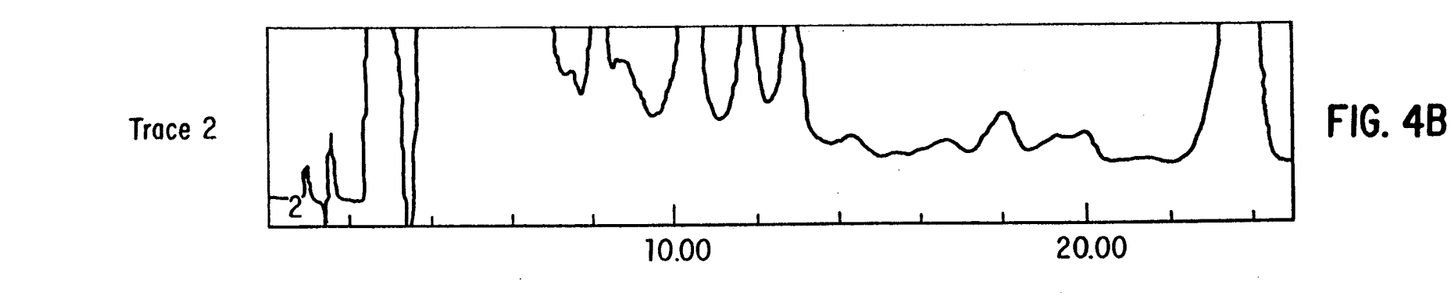
Figure 4C:
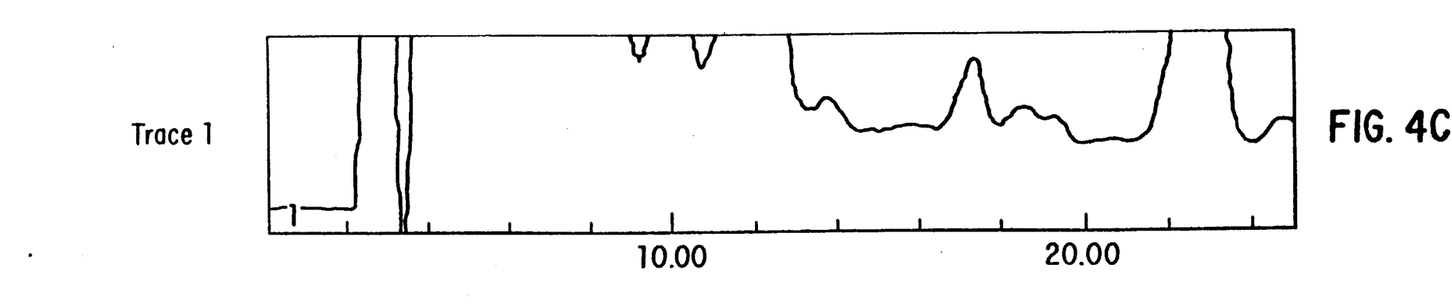

Once well-dispersed liquid cultures were obtained, taxol was produced in the following way. Cultures were inoculated into fresh medium by pipetting known volumes into fresh medium such that the inoculation density was 1 part mother culture to 10 parts fresh medium. Cultures were incubated with shaking under the conditions described above, and after 21 days the spent medium was collected. The spent medium was concentrated to dryness in vacuo and taxol was extracted and detected by HPLC (see FIG. 4).

As shown in FIG. 4, trace 1, the Taxus extract contained a number of peaks which eluted at about the same place as a taxol standard. Trace 2 is an HPLC showing the separation of a 3:1 mixture of Taxus extract and taxol standard. It can be seen that the shoulder which eluted just before 20.00 minutes has increased in size. When a 1:1 mixture of Taxus extract and taxol standard were separated, this shoulder increased further, thus confirming the presence of taxol. Also evident are other taxane-ring containing compounds such as cephalomannine.

Having now fully described this invention, it will be understood by those of skill in the art that it can be performed within any wide range of equivalent modes of operation as well as other parameters without affecting the scope of the invention or any embodiment thereof.

What is claimed is:

1. A method of producing taxane ring-containing compounds from somatic embryos of Taxus which are capable of producing said compounds, comprising the steps of:
   culturing embryos from the genus Taxus in a culture medium under conditions which produce somatic embryos; and
   isolating said taxane ring-containing compounds from said embryos or said medium.

2. A method of producing taxane ring-containing compounds from embryogenic tissue cultures of Taxus which are capable of producing said compounds, comprising the steps of:
   culturing embryos from the genus Taxus in a culture medium under conditions which produce embryogenic tissue; and
   isolating said taxane ring-containing compounds from said embryogenic tissue or said medium.

3. The method of claim 1 or 2, wherein said explants are cultured in liquid medium and dispersed by shaking.

4. The method of claim 1 or 2, wherein said explants are from *T. x media, T. baccata* or *T. brevifolia*.

5. The method of claim 1 or 2, wherein said explants are from *T. brevifolia*.

6. The method of claim 1 or 2, wherein said taxane ring-containing compound is taxol.

* * * * *

UNITED STATES PATENT AND TRADEMARK OFFICE
CERTIFICATE OF CORRECTION

PATENT NO. : 5,310,672
DATED : May 10, 1994
INVENTOR(S) : Wann et al

It is certified that error appears in the above-indentified patent and that said Letters Patent is hereby corrected as shown below:

Title Page:
Item [54] in the title, change "EMBRYOGENISIS" to --EMBRYOGENESIS--.
Item [56] References Cited, change "Embryogensis" to --Embryogenesis--;
under "Other Publications," column 2, line 14, change "Durzen" to --Durzan--;

bridging lines 14-15, change "Polyembryogenes is" to --Polyembryogenesis--;
      line 22, change "Lobiolly" to --Loblolly--; and
      line 27, change "Orgin" to --Origin--.

Page 2 of the facing page, under "Other Publications," column 1, line 5, change "*bot.*" to --*Bot.*--;

line 12, change "*Trees3*" to --*Trees 3*--; and
      line 15, change "3914 42" to --39-42--.

Column 2, line 14, change "Researches" to --Researchers--;
      line 25, change "Heedelberg" to --Heidelberg--;
      line 53, change "detention" to --definition--; and
      line 62, change "Tisseral" to --Tisserat--.

Column 3, line 23, change "*Sci*62" to --*Sci. 62*--; and
      line 36, change "Schewmaker" to --Shewmaker--.

Column 5, line 48, change "consist" to --consists--.

UNITED STATES PATENT AND TRADEMARK OFFICE
CERTIFICATE OF CORRECTION

PATENT NO. : 5,310,672
DATED : May 10, 1994
INVENTOR(S) : Wann et al

It is certified that error appears in the above-indentified patent and that said Letters Patent is hereby corrected as shown below:

Column 6, line 45, change "Tween-20 TM" to --Tween-20™--;
    line 46, change "effecting" to --affecting--; and
    bridging lines 64 and 65, change "will can" to --can--.
Column 7, line 47, change "for" to --be--.
Column 10, line 8, change "act" to --acts--;
    line 27, change "maybe" to --may be --; and
    line 49, change "Tween 20TM" to --Tween 20™--.
Column 12, line 24, change "(See Below)" to --(See Figure 1)--.
Column 14, line 10, change "explants" to --embryos--;
    line 12, change "explants" to --embryos--; and
    line 14, change "explants" to --embryos--.

Signed and Sealed this

Eighteenth Day of April, 1995

BRUCE LEHMAN

Attest:

Attesting Officer

Commissioner of Patents and Trademarks